(12) United States Patent
Tharp

(10) Patent No.: US 6,543,753 B1
(45) Date of Patent: Apr. 8, 2003

(54) AIR DIFFUSER MEMBRANE TREATED WITH BIOCIDE

(75) Inventor: Charles E. Tharp, Columbia, MO (US)

(73) Assignee: Environmental Dynamics, Inc., Columbia, MO (US)

( * ) Notice: Subject to any disclaimer, the term of this patent is extended or adjusted under 35 U.S.C. 154(b) by 0 days.

(21) Appl. No.: 09/976,498

(22) Filed: Oct. 12, 2001

(51) Int. Cl.[7] ................................................ B01F 3/04
(52) U.S. Cl. ............ 261/122.2; 261/124; 261/DIG. 70; 210/220
(58) Field of Search ........................... 261/122.1, 122.2, 261/124, DIG. 70, DIG. 46; 210/220

(56) References Cited

U.S. PATENT DOCUMENTS

| | | | |
|---|---|---|---|
| 3,857,910 A | | 12/1974 | Day |
| 3,977,606 A | | 8/1976 | Wyss |
| 4,489,016 A | * | 12/1984 | Kriebel .................. 261/122.2 |
| 4,770,790 A | | 9/1988 | Oberhofer |
| 4,851,163 A | | 7/1989 | Stanton et al. |
| 5,006,267 A | | 4/1991 | Vaughn et al. |
| 5,059,358 A | * | 10/1991 | Tharp .................. 261/122.2 |
| 5,093,047 A | * | 3/1992 | Zeppenfeld ............. 261/122.1 |
| 5,102,547 A | | 4/1992 | Waite et al. |
| 5,679,399 A | | 10/1997 | Shlenker et al. |
| 5,800,705 A | * | 9/1998 | Downs .................. 210/220 |
| 6,171,496 B1 | * | 1/2001 | Patil ..................... 210/484 |
| 6,254,775 B1 | | 7/2001 | McElvaney |
| 6,264,176 B1 | | 7/2001 | Dickman et al. |
| 6,344,147 B1 | * | 2/2002 | Meyer .................. 261/122.2 |
| 6,355,096 B1 | * | 3/2002 | Schmidtke .............. 261/124 |
| 6,406,005 B1 | * | 6/2002 | Lawson et al. ...... 261/DIG. 70 |
| 6,420,455 B1 | * | 7/2002 | Landgrebe et al. ......... 523/122 |
| 6,425,821 B1 | * | 7/2002 | Koerber et al. ............ 454/296 |

FOREIGN PATENT DOCUMENTS

| | | |
|---|---|---|
| DE | 003744608 | 7/1989 |
| JP | 0073857 | 6/1978 |

* cited by examiner

Primary Examiner—C. Scott Bushey
(74) Attorney, Agent, or Firm—Shook, Hardy & Bacon L.L.P.

(57) ABSTRACT

A fine bubble diffuser membrane used in the aeration of wastewater is treated with biocide to inhibit growth and accumulation of biological materials on the membrane. The membrane may be constructed of EPDM rubber or urethane. The biocide may be carbolic acid either dispersed throughout the membrane or applied as a coating on the surface of the membrane exposed to the wastewater. The membrane is a flexible and elastic structure impervious to liquid and provided with slits that close to prevent wastewater inflow in the absence of aeration and open in response to aeration pressure to discharge air into the wastewater.

16 Claims, 1 Drawing Sheet

AIR DIFFUSER MEMBRANE TREATED WITH BIOCIDE

FIELD OF THE INVENTION

This invention relates generally to the aeration of wastewater and more particularly to an air diffuser membrane that is treated with a biocidal agent which inhibits biological growth on the membrane surface.

BACKGROUND OF THE INVENTION

Flexible membrane diffusers are in widespread use for the aeration and mixing of wastewater. By way of example, U.S. Pat. No. 4,960,546 to Tharp discloses a flexible membrane diffuser that is sleeved onto a rigid tubular diffuser body to provide a construction that has achieved considerable popularity. The membrane collapses on the diffuser body and fits closely around it when no air is being supplied by the blower to the piping of the aeration system. When the aeration is active, air is supplied through the piping to the diffuser body and enters the inside of the membrane through ports in the diffuser body. The air pressure causes the membrane to expand as it receives the air.

This type of diffuser membrane is provided with a large number of aeration slits which are closed when the membrane is collapsed on the diffuser tube in the absence of air pressure. The wastewater cannot seep into the aeration piping because the closed slits do not provide access and the membrane is impervious to liquid. However, when the air is turned on and the membrane expands, the slits open and allow the air to discharge into the wastewater in the form of fine bubbles. Such small bubbles are advantageous from an efficiency standpoint because their relatively small volume to surface area ratio results in more efficient aeration. The slits are controlled apertures because the extent to which they open varies with varying air pressure.

In addition to use in tubular diffuser systems, flexible membranes have been used in other diffuser configurations, including disk type diffusers. The membrane is used in this application as a flat disk member which covers the diffuser plenum in the body of the diffuser and discharges air in fine bubbles in much the same manner as in the case of tubular diffusers.

Flexible membrane diffusers are typically constructed of EPDM rubber or urethane. These materials exhibit the necessary structural characteristics. They are also flexible and elastic and thus able to meet the operational requirements for the membrane in these aspects.

Although flexible membrane diffusers have been satisfactory for the most part, they can be susceptible to biological fouling, especially when used in relatively severe applications where biological growth is promoted due to the conditions of the wastewater. In harsh wastewater environments, it is not uncommon for algae and other biological material to build up on the surface of the membrane, often quickly and to a significant extent. When biological growth accumulates on the membrane, there is a marked increase in the size of the bubbles that are released into the wastewater, as the fine bubbles tend to merge in the biological growth and create larger bubbles which are finally released into the liquid. As a result, the efficiency of the oxygen transfer to the wastewater suffers a significant reduction.

Although there have been proposals made to apply biocides to other types of membranes, such as filtration membranes which are permeable, impermeable flexible membrane diffusers have not been treated with biocidal agents. U.S. Pat. No. 5,102,547 to Waite et al. discloses a filter membrane that is treated with biostatic or biocidal agents. Because the membrane serves as a filter, it is necessarily permeable to liquids in order to allow liquids to pass through it for filtration of the liquid. This type of filter membrane is clearly of no use in treating wastewater and can only be used in clean water environments because it would quickly become fouled by solids in wastewater or other liquids having suspended solids. Similarly, U.S. Pat. No. 5,106,267 to Vaughn et al. is directed only to the biocidal treatment of porous or permeable membranes that have no applicability for aeration and are not useful in wastewater applications.

SUMMARY OF THE INVENTION

The present invention is directed to a flexible and elastic diffuser membrane which is used in the aeration of wastewater and which is impregnated or otherwise treated with biocide in order to resist biological accumulations on the membrane surface.

In accordance with the invention, a diffuser membrane is preferably constructed of a material such as EPDM rubber or urethane. The structural materials of the membrane are preferably mixed with a biocide such as carbolic acid which is thereby dispersed throughout the membrane structure. Alternatively, the membrane can be coated with biocide on the surface which is exposed to wastewater when the membrane is in service submerged in the wastewater.

In either case, the membrane is a flexible and elastic structure which is slitted to provide controlled apertures for the release of fine bubbles of air into the wastewater for aeration and mixing of the wastewater. The membrane may be closely sleeved on a rigid tubular diffuser body which is ported in order to apply air to the inside of the membrane. In the absence of air pressure, the membrane collapses tightly on the diffuser body and the slits are closed to prevent entry of wastewater into the piping of the aeration system. When air is applied, it expands the membrane and opens the slits to allow the discharge of air into the wastewater in the form of fine bubbles.

The membrane may take other forms, including the form of a disk diffuser in which a plenum is covered by a flat membrane. When air is supplied to the plenum, the membrane expands and the slits open for discharge of the air into the wastewater.

The treatment of the diffuser membrane with biocide inhibits the growth and accumulation of algae and other biological substances on the membrane. This has the beneficial effect of preventing biological growth from causing the air bubbles to increase in size, often dramatically, as can occur in wastewaters that have severe conditions conducive to biological growth. Consequently, the biocidally treated membrane of the present invention retains its ability to produce fine bubbles and thus continues to operate near peak efficiency even in harsh or severe wastewater conditions.

Other and further objects of the invention, together with the features of novelty appurtenant thereto, will appear in the course of the following description.

DESCRIPTION OF THE DRAWING

In the accompanying drawing which forms a part of the specification and is to be read in conjunction therewith and in which like reference numerals are used to indicate like parts in the various views.

DETAILED DESCRIPTION OF THE INVENTION

Figure 1:
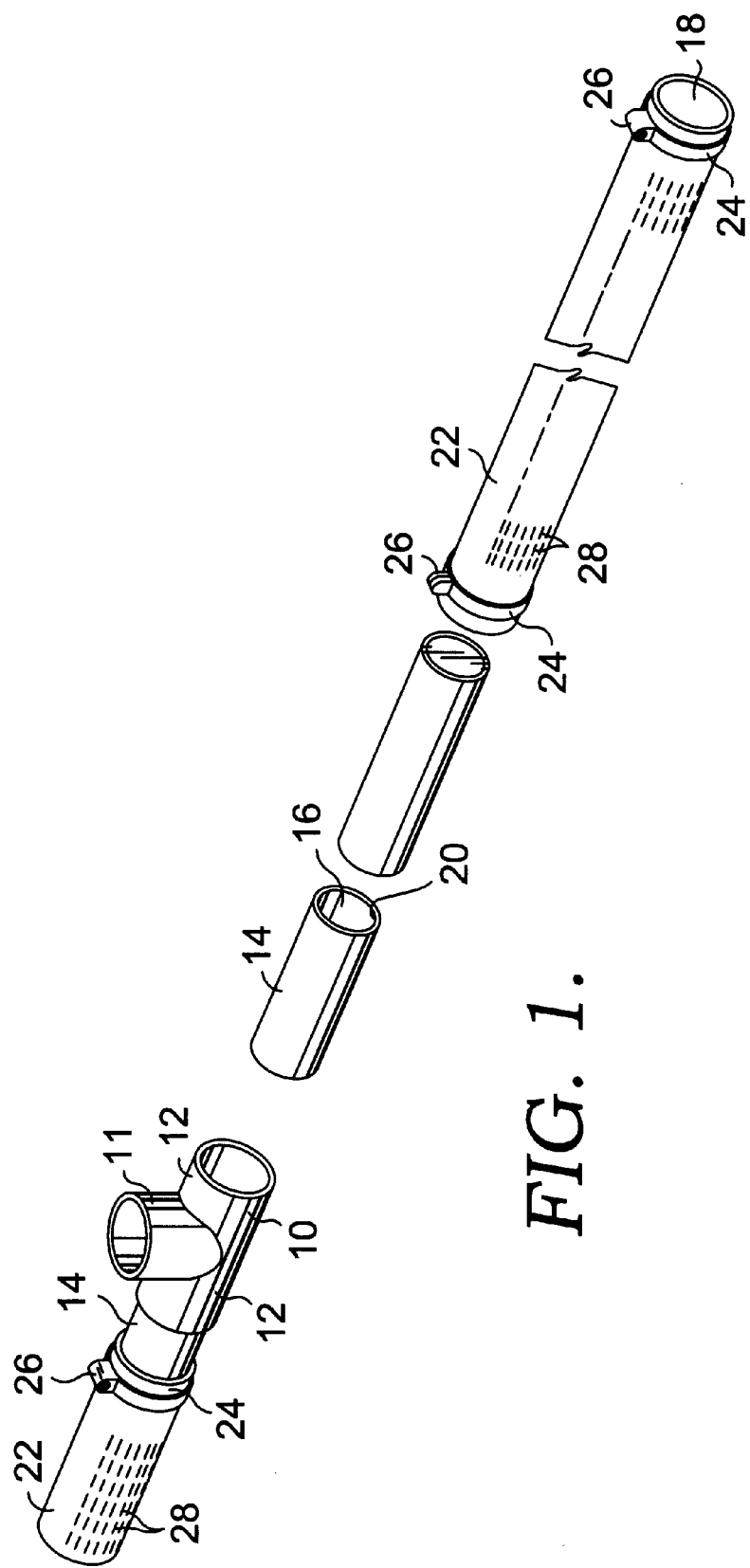
FIG. 1 is an exploded perspective view of a tubular air diffuser arrangement of a type that may incorporate a biocidally treated diffuser membrane constructed according to a preferred embodiment of the present invention, with the break lines indicating continuous length.

The present invention is directed to a flexible and elastic diffuser impermeable membrane which is biocidally treated in order to inhibit biological growth and which is used in an aeration system that operates to aerate and mix wastewater. One type of aeration system with which the biocidally treated membrane of the present invention may be used is disclosed in U.S. Pat. No. 4,960,546 which issued on Oct. 2, 1990 to Charles E. Tharp, which patent is incorporated by reference.

As disclosed in the aforementioned Tharp patent and shown in FIG. 1 of this application, air is supplied by the aeration system to a tee fitting 10 having a vertically oriented inlet 11 which receives the air and a pair of oppositely directed outlets 12 which discharge the air in a horizontal direction. Secured in each of the outlets 12 is an elongated tubular diffuser body 14 which is preferably constructed of a rigid plastic and has a hollow interior 16. A plug 18 may plug the outer end of each diffuser body 14 or may be secured at an intermediate location along the length of each diffuser body, as desired. Each diffuser body 14 preferably has a cylindrical shape and is provided with a plurality of ports such as the port 20 through which air passes from the interior 16 of the diffuser body to its exterior.

In accordance with the present invention, each diffuser body 14 is provided with a flexible membrane diffuser 22 which is sleeved over the diffuser body 14 and suitably secured to it, as by hose clamps 24 equipped with conventional fasteners 26. Each membrane 22 has a wall which is a cylindrical structure that is flexible and elastic. The membrane 22 fits closely on the diffuser body 14 and is collapsed tightly on the exterior surface of the diffuser body when air is not being applied to the diffuser body 14 by the aeration system.

The membrane 22 is preferably constructed of a material such as EPDM rubber or urethane. In accordance with the present invention, the structural components of the membrane 22, which may constitute a suitable polymer, carbon black and calcium carbonate, may be mixed with a biocide that, due to the mixing process, is dispersed throughout the wall of membrane 22 in a relatively uniform manner. The biocide is preferably carbolic acid or phenol. By way of example, the biocide may be a compound that is commercially available from Clariant Corporation of Charlotte, N.C. under the trademark NIPACIDE which is an antimicrobial agent. Other suitable biocidal agents are also contemplated.

By mixing the biocide with the other components of the membrane, the biocide is dispersed throughout the EPDM rubber matrix. The EPDM rubber, in which the biocide is dispersed, is preferably molded or otherwise suitably formed into the shape desired for the membrane 22. The membrane material is impervious to liquid.

Alternatively, the membrane 22 can be molded or otherwise formed, and the biocide can then be applied as a coating on the exterior surface of the membrane 22 which is the surface exposed to the wastewater when the membrane is in service submerged in the wastewater.

After the biocide has been applied to the membrane 22, either by dispersing it throughout the membrane or applying it as a coating on the surface of the membrane, and the membrane has been molded or otherwise formed, a plurality of small aeration slits 28 are formed through the membrane wall. The slits 28 serve as controlled aeration apertures which are closed when the membrane 22 is sealed against the outer surface of the diffuser body 14 in the absence of air pressure. However, when air is supplied to the interior of the membrane through the ports 20 of the diffuser body 14, the membrane 22 expands outwardly away from the diffuser body, as permitted by its flexibility. Then, the aeration slits 28 open and allow the air to pass through them and discharge into the wastewater in the form of a fine bubbles resulting from the small size of the slits 28. When the aeration system is deactivated and the air pressure is withdrawn, the elasticity of the membrane 22 causes it to collapse again tightly on the diffuser body 14, thereby again closing the slits 28 and sealing the diffuser against the outside surface of the diffuser body. Consequently, the wastewater is unable to enter the diffuser body 14 and the distribution piping of the aeration system because the openings 28 do not provide access for the wastewater and the membrane 22 is impervious to liquid.

The treatment of the membrane 22 with biocide, whether it is dispersed throughout the membrane or coated on its surface, inhibits the growth and buildup of algae and other biological material on the membrane surface. A membrane that is not treated with biocide can be subject to accumulation of biological growth which traps the fine bubbles discharged through the slits 28 and causes them to merge and form larger bubbles before they are released from the biological growth into the wastewater. Large bubbles result in less efficient aeration because the bubble volume to surface area ratio is larger with larger bubbles, and the oxygen transfer to the wastewater suffers accordingly. Thus, by using the biocidally treated membrane 22 of the present invention, the efficiency of the oxygen transfer remains intact because the growth and buildup of biological materials is inhibited by the biocide.

In the case of a biocidal agent that is dispersed throughout the cylindrical wall of the membrane 22, when the membrane has been in service for an extended time period, the biocidal agent may leach out of the membrane. However, the biocidal agent that is initially located deeper within the membrane tends to migrate toward the surface and thus remains effective in inhibiting biological growth for a prolonged period of time. In the case of the biocide that is coated on the surface of the membrane, the biocide may remain effective for a prolonged period depending upon a number of factors that vary with the construction and configuration of the diffuser and the conditions of the wastewater.

The present invention contemplates biocially treated membranes having configurations other than the tubular or cylindrical configuration of the membrane 22. By way of example, disk type diffusers having a diffuser body presenting a plenum that is covered by a disk-shaped membrane can make use of a biocidally treated membrane in accordance with the present invention. With this type of diffuser, the membrane collapses to a flat condition covering the plenum in the absence of air pressure, with the aeration slits closing to prevent seepage of wastewater into the plenum and the aeration piping of the system. When air pressure is applied, the air flows to the plenum and causes the membrane to expand or bulge outwardly, thereby opening the aeration slits and allowing the air to discharge into the wastewater in the form of fine bubbles which are efficient for the aeration and mixing function of the aeration system. The effect of the biocidal agent in connection with a membrane of a disk type diffuser is substantially the same as in the case with a tubular membrane such as a membrane 22. References to elasticity herein means the tendency of the material to revert to its original shape after having been deformed.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

Having thus described the invention, what is claimed is:

1. A diffuser membrane for applying air to wastewater for aeration of the wastewater, said membrane comprising:

a flexible and elastic membrane wall which is impervious to the passage of liquid therethrough;

a plurality of aeration slits in said membrane wall which are normally closed to prevent passage of the wastewater therethrough but which open when air under pressure is applied to said membrane wall so that air can pass through said slits into the wastewater; and a biocide applied to said membrane wall to resist biological growth thereon.

2. A membrane as set forth in claim 1, wherein said membrane wall comprises EPDM.

3. A membrane as set forth in claim 2, wherein said biocide comprises carbolic acid.

4. A membrane as set forth in claim 3, wherein said carbolic acid is dispersed throughout said EPDM.

5. A membrane as set forth in claim 3, wherein said carbolic acid is coated on said EPDM on a surface thereof exposed to the wastewater.

6. A membrane as set forth in claim 1, wherein said membrane wall comprises urethane.

7. A membrane as set forth in claim 6, wherein said biocide comprises carbolic acid.

8. A membrane as set forth in claim 7, wherein said carbolic acid is dispersed throughout said urethane.

9. A membrane as set forth in claim 7, wherein said carbolic acid is coated on said urethane on a surface thereof exposed to the wastewater.

10. A membrane as set forth in claim 1, wherein said biocide comprises carbolic acid.

11. A membrane as set forth in claim 10, wherein said carbolic acid is dispersed throughout said membrane wall.

12. A membrane as set forth in claim 10, wherein said carbolic acid is coated on said membrane wall on a surface thereof exposed to the wastewater.

13. A membrane as set forth in claim 1, wherein said biocide is dispersed throughout said membrane wall.

14. A membrane as set forth in claim 1, wherein said biocide is coated on said membrane wall on a surface thereof exposed to the wastewater.

15. A membrane construction for use in the application of air to wastewater, comprising:

a tubular membrane impervious to the passage of the wastewater therethrough and constructed of a flexible and elastic material to allow the membrane to be sleeved closely on a diffuser body ported to apply air to the inside of the membrane;

a plurality of slits through said membrane normally closed to prevent passage of wastewater into the membrane, said slits opening upon application of air under pressure to the inside of the membrane to allow the air to discharge into the wastewater; and a biocide on said membrane for resisting biological growth thereon.

16. An air diffuser for submergence in wastewater to apply air for treatment of the wastewater, said diffuser comprising:

a rigid diffuser body having a tubular shape and a hollow interior for receiving air to be applied to the wastewater, said diffuser body having a port for discharging air from said interior;

a tubular membrane constructed of a flexible and elastic material impervious to passage of wastewater therethrough, said membrane being sleeved on said diffuser body and being normally collapsed thereon but expanded when air under pressure is supplied to the membrane through said port;

a plurality of aeration slits in said membrane, said slits being closed when said membrane is collapsed on said diffuser body and opened to discharge air when said membrane is expanded by air supplied thereto through said port; and said membrane being treated with biocide for resisting biological growth thereon.

\* \* \* \* \*